(12) United States Patent
Cox

(10) Patent No.: US 10,779,986 B2
(45) Date of Patent: Sep. 22, 2020

(54) DEVICE FOR CLEANING A STOMA IN A HUMAN OR ANIMAL BODY

(71) Applicant: Stomydo B.V., Reuver (NL)

(72) Inventor: Peter Jacobus Marie Cox, Reuver (NL)

(73) Assignee: STOMYDO B.V., Reuver (NL)

( * ) Notice: Subject to any disclaimer, the term of this patent is extended or adjusted under 35 U.S.C. 154(b) by 574 days.

(21) Appl. No.: 15/517,566

(22) PCT Filed: Sep. 30, 2015

(86) PCT No.: PCT/NL2015/050678
§ 371 (c)(1),
(2) Date: Apr. 7, 2017

(87) PCT Pub. No.: WO2016/056897
PCT Pub. Date: Apr. 14, 2016

(65) Prior Publication Data
US 2017/0246025 A1    Aug. 31, 2017

(30) Foreign Application Priority Data
Oct. 9, 2014 (NL) .................................. 2013602

(51) Int. Cl.
*A61F 5/442* (2006.01)
*A61B 90/80* (2016.01)
*A61F 5/445* (2006.01)

(52) U.S. Cl.
CPC .............. *A61F 5/442* (2013.01); *A61B 90/80* (2016.02); *A61F 5/445* (2013.01)

(58) Field of Classification Search
CPC combination set(s) only.
See application file for complete search history.

(56) References Cited

U.S. PATENT DOCUMENTS 2,221,321 A * 11/1940 Foron ...................... A61F 5/445
604/337
2,759,477 A *  8/1956 Mains ................... A61F 5/4408
604/343

(Continued)

FOREIGN PATENT DOCUMENTS

FR           685816 A    7/1930
FR          1014580 A    8/1952
WO    WO 1998024387 A1  6/1998

OTHER PUBLICATIONS

International Search Report for International Patent Application No. PCT/NL2015/050678, dated Mar. 2, 2016.

*Primary Examiner* — Tatyana Zalukaeva
*Assistant Examiner* — Guy K Townsend
(74) *Attorney, Agent, or Firm* — Shumaker, Loop & Kendrick, LLP

(57) ABSTRACT

The invention relates to a device for cleaning a stoma in a human or animal body. The object of the invention is to provide a device as described in the introduction which completely abuts the skin's surface, irrespective of the location of the stoma on the body and irrespective of the person's or animal's build. In order to achieve that object, the device is according to the invention characterised in that the circular contact edge of the container is provided with a circular flexible collar comprising at least a first circumferential edge and a second circumferential edge, which first circumferential edge and second circumferential edge enclose an air chamber when placed on the body.

9 Claims, 4 Drawing Sheets

(56) References Cited

U.S. PATENT DOCUMENTS

| | | | | |
|---|---|---|---|---|
| 3,042,041 A * | 7/1962 | Jascalevich | A61M 27/00 | 604/277 |
| 3,910,274 A * | 10/1975 | Nolan | A61F 5/442 | 604/277 |
| 4,326,521 A * | 4/1982 | Marsan | A61F 5/445 | 604/342 |
| 4,543,095 A * | 9/1985 | Jensen | G01F 1/065 | 604/246 |
| 4,596,566 A * | 6/1986 | Kay | A61F 5/445 | 604/176 |
| 4,668,227 A * | 5/1987 | Kay | A61B 90/70 | 134/57 R |
| 6,245,049 B1 * | 6/2001 | Samuelsson | A61F 5/445 | 604/276 |
| 6,840,923 B1 * | 1/2005 | Lapcevic | A61F 5/442 | 604/319 |
| 7,160,274 B2 * | 1/2007 | Ciok | A61F 5/442 | 604/305 |
| 7,216,651 B2 * | 5/2007 | Argenta | A61M 1/0088 | 128/897 |
| 7,842,018 B2 * | 11/2010 | Schena | A61F 5/445 | 604/334 |
| 2004/0054339 A1 * | 3/2004 | Ciok | A61F 5/442 | 604/334 |
| 2006/0253090 A1 * | 11/2006 | Bradley | A61F 5/445 | 604/334 |
| 2010/0241092 A1 * | 9/2010 | Nguyen-DeMary | A61P 31/00 | 604/336 |
| 2011/0106032 A1 * | 5/2011 | Kratky | A61F 5/445 | 604/337 |
| 2012/0215188 A1 * | 8/2012 | Salama | A61F 5/448 | 604/335 |
| 2013/0197458 A1 * | 8/2013 | Salama | A61F 5/4405 | 604/335 |
| 2013/0304008 A1 * | 11/2013 | Hanuka | A61F 5/4405 | 604/334 |
| 2017/0246025 A1 * | 8/2017 | Cox | A61B 90/80 | |

* cited by examiner

DEVICE FOR CLEANING A STOMA IN A HUMAN OR ANIMAL BODY

The invention relates to a device for cleaning a stoma in a human or animal body.

Such a device is known, for example from International patent application WO98/24387A1.

A stoma is an artificial opening in the human or animal body and can function to discharge faecal matter or urine or bile or to facilitate the respiration. In the latter case the term "tracheostoma" is used. Where in the present application the term "stoma" is used, however, a stoma is meant which is placed to facilitate the discharge of faecal matter and urine. In such situations, the term "ileostoma" is used to indicate a stoma that is connected to the small intestine, or "colostoma", to indicate a stoma that is connected to the large intestine, or "urostoma", to indicate a stoma that functions to discharge urine.

Usually the stoma wound is covered by a stoma dressing (also called collecting material or skin flange), possibly provided with an ostomy pouch for collecting the faecal matter. It will be understood that said dressing (or skin flange) must be replaced at regular intervals, on which occasion the stoma wound (opening must be cleaned.

A device disclosed in WO98/24387A1 is intended for cleaning or rinsing the stoma and the surrounding skin with lukewarm water. This usually improves the quality of life for the patient. People who have a stoma generally have a limited social life and, out of shame or out of necessity, they hardly take part in society anymore because the stoma wound sometimes leads to awkward situations. Think in that connection of leakage of the ostomy pouch (more in particular of the flange, with leakage taking place along the skin), as a result of which faecal matter is released.

The device shown in WO98/24387A1 consists of a flask-like container of a transparent material, such as plastic or glass. The flask is placed with its circumferential edge on the skin of the person (or animal) in question, with the flask enclosing the stoma. Via a first inlet opening, which can be connected to a faucet, rinse water having the desired temperature is led into the flask-like container, which rinse water can be discharged to a water drain or toilet drain via an outlet opening after rinsing or cleaning of the stoma wound and the surrounding skin has taken place.

Although the circumferential wall of the flask-like container known from WO98/24387A1 is elastic for reasons of user-friendliness, the known device has the drawback that the container leaks along its circumferential edge, in particular in the case of a high water supply/pressure, and also in the case of humans and animals with a heavy build.

In the above situations the skin surface is not flat enough, so that a fully leak-proof connection of the known flask-like container to the skin cannot be realised.

The object of the invention is to obviate the above drawback and to provide a device as described in the introduction which completely abuts the skin's surface, irrespective of the location of the stoma on the body and irrespective of the person's or animal's build.

In order to achieve that object, the device is according to the invention characterised in that the circular contact edge of the container is provided with a circular flexible collar comprising at least a first circumferential edge and a second circumferential edge, which first circumferential edge and second circumferential edge enclose an air chamber when placed on the body.

The construction of the circular flexible collar having a first circumferential edge and a second circumferential edge has the advantage that once the container is placed on the skin (and around the stoma wound) and the container with its circular flexible collar is lightly pressed against the skin, air can escape into the outside environment from the air chamber enclosed by the two circumferential edges (and the skin's surface) into the outside environment. As a result, an underpressure (slight vacuum) is created in the air chamber, which resists movement of the container during the cleaning session but which above all prevents leakage of rinse water along the circumferential edge of the container.

More in particular, the first circumferential edge abuts the body substantially at right angles when placed on the skin's surface, thus realising a first moisture seal. Because the second circumferential edge is further configured as a folded-over flanged edge, which abuts the skin's surface when placed on the body, on the one hand an additional seal is realised, but more importantly the flat abutting orientation of the second circumferential edge against the skin's surface allows a small amount of trapped air to escape from the enclosed air chamber as a result of the container being lightly pressed against the skin. The latter creates a slight underpressure in the air chamber enclosed by the two circumferential edges (and the skin's surface), so that shifting and leakage along the two circumferential edges cannot occur.

In a specific embodiment, the second circumferential edge surrounds the first circumferential edge. In this embodiment, the second circumferential edge can be regarded as an outer circumferential edge, which outer circumferential edge surrounds the first, inner circumferential edge.

Similarly, in another embodiment the first circumferential edge may surround the second circumferential edge. The second circumferential edge can in that case be regarded as an inner circumferential edge, therefore, which inner circumferential edge is surrounded by the first, outer circumferential edge.

In both embodiments an effective seal of the stoma wound is realised.

In a further aspect of the invention, the inlet opening has an outflow surface provided with several openings, which openings are arranged in a concentric ring along the outer circumference of the outflow surface. In this way the rinse water is not aimed directly at the stoma wound—in contrast to the device known from WO98/24387A1—but directly beside it at the skin that concentrically surrounds the stoma wound. This has the advantage that on the one hand the soiled skin is directly cleaned. An additional advantage of this embodiment of the inlet opening is that the skin surrounding the stoma wound is massaged by the water jets, which stimulates the blood flow of the skin and significantly reduces the risk of necrosis or irritation of the skin. This, too, significantly enhances the stoma patient's comfort.

In addition to that, besides the massage effect of the water jets also the vacuum realised by the circular flexible collar has a stimulating effect on the skin.

The invention will now be explained in more detail with reference to a drawing, in which.

For a better understanding of the invention, like parts will be indicated by the same numerals in the following description of the figures.

Figure 1:
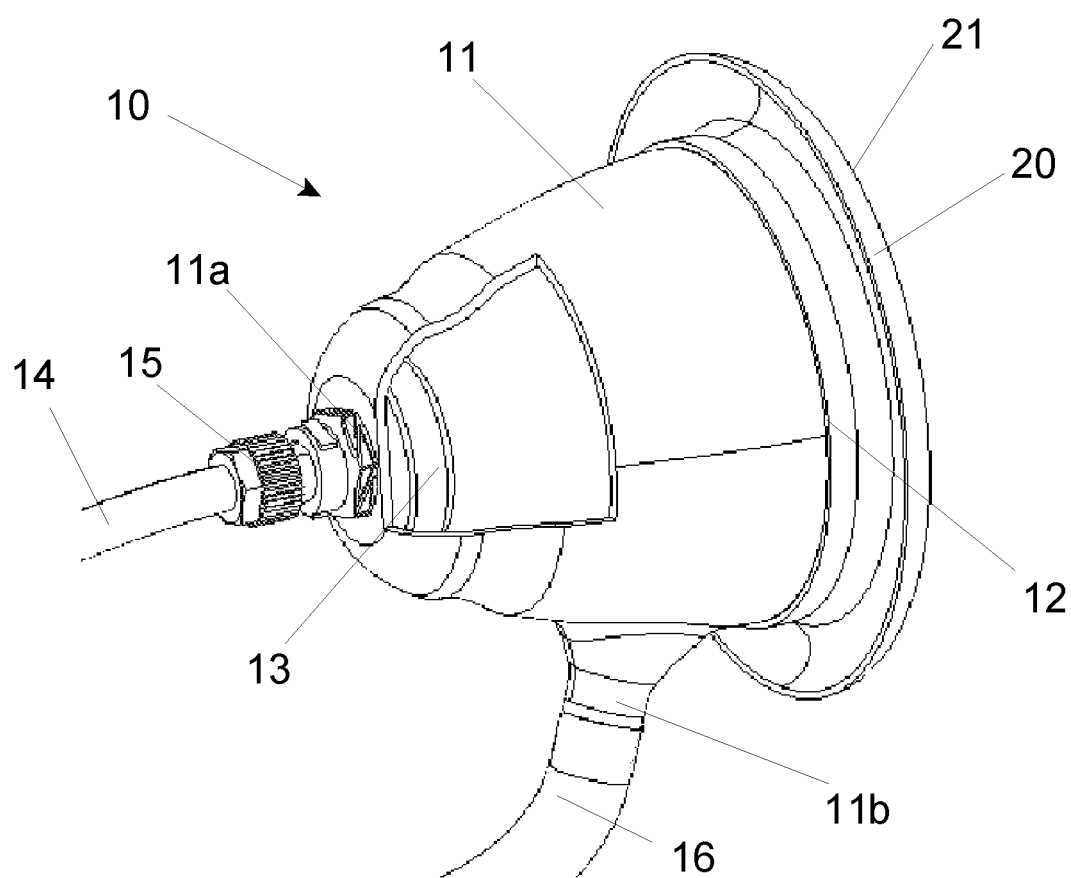
FIG. 1 is a view of an embodiment of a device according to the invention.

FIG. 1 shows an embodiment of a device according to the invention for cleaning a stoma. The device is indicated by reference numeral 10 and is in part made up of a flask-like container 11. The flask-like container 11 is preferably made of a transparent material, such as plastic or glass. This makes it easy for the patient to clean the device after every cleaning session. The flask-like container 11 has a circumferential edge 12, which is provided with a circular flexible collar 20. The latter can be placed on the patient's skin with its circumferential edge 21.

The flexible collar 20 is detachably provided on the edge 12, so as to make it possible to clean the two parts.

Reference numeral 11a indicates an inlet opening intended for supplying water into the flask-like container 11. The inlet opening 11a is connected to a hose 14 via a coupling 15, which hose can be connected to a water source, such as a faucet (not shown).

In this way the user of the device according to the invention, usually be stoma patient, can connect the device to a faucet and control the temperature of the rinse water himself, which rinse water can subsequently be led into the container 11 via the hose 14.

The inlet opening 11a is provided with a nozzle 13 having an outflow surface 13a (see also FIGS. 2 and 3) that is provided with several outlet openings.

The container 11 is also provided with an outlet opening 11b, to which a discharge hose 16 is connected for the discharge of dirty rinse water to a drain hole in a washbasin or shower or toilet.

Using the device 10 according to the invention, the patient must connect the hose 14 to a water source (faucet) and connect or place the discharge hose 16 to/in a drain. Once the desired water temperature has been set, the container 10 must be placed on the skin's surface and around the stoma wound with the circumferential edge 21 of the circular flexible collar 20, after which cleaning of the stoma and the surrounding skin can take place.

Figure 2:
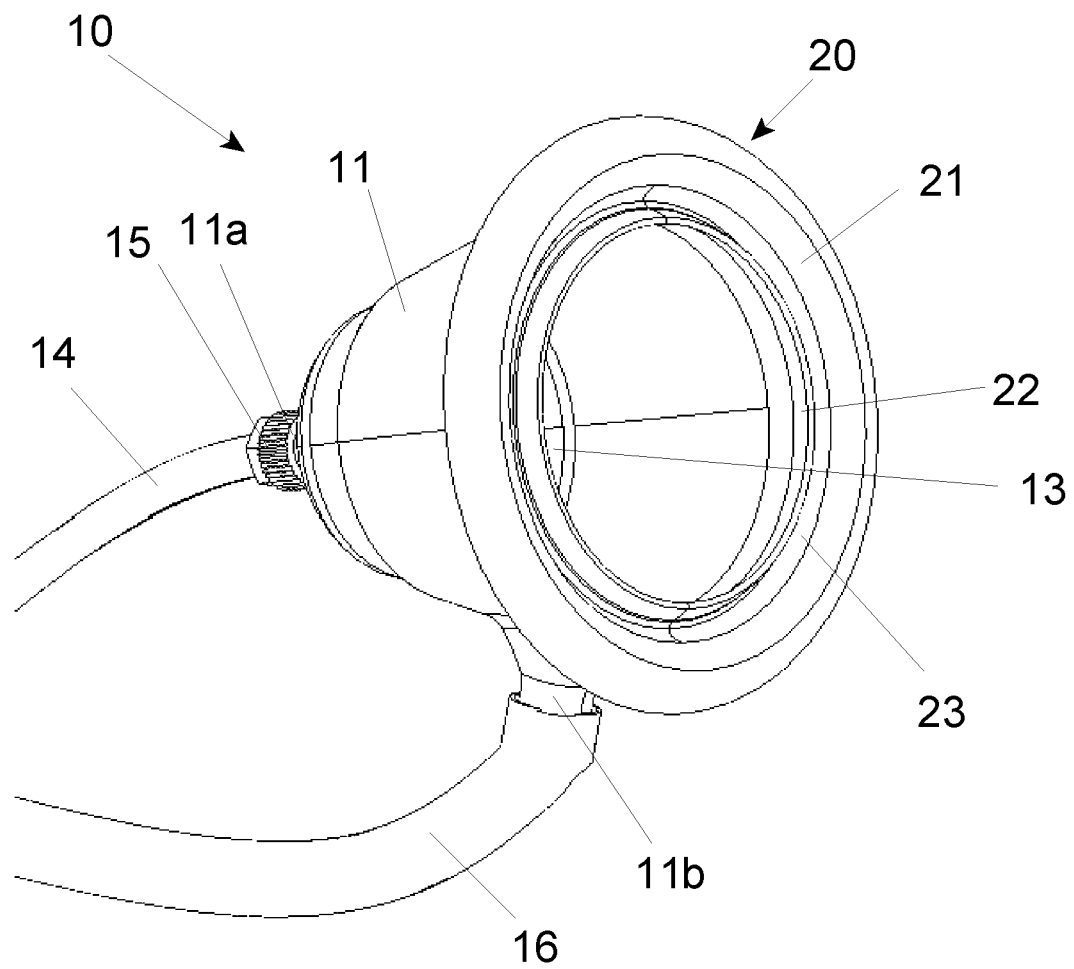
FIG. 2 is another view of the embodiment shown in FIG. 1.

FIG. 2 shows a front view of the rinsing device shown in FIG. 1. In FIG. 2 the circular flexible collar 20 is disclosed in more detail. As shown, the circular flexible collar 20 comprises a first circumferential edge 22, which preferably abuts the skin's surface substantially at right angles when placed on the body. The circumferential edge 22 may be slightly curved, if desired. The circular flexible collar 20 also has a second circumferential edge 21, which is preferably configured as a folded-over flanged edge which lies substantially flat against the skin's surface.

In this embodiment, the first circumferential edge 22, which abuts the skin substantially at right angles, is surrounded by the second, folded-over circumferential edge 21, which lies substantially flat against the skin's surface. In this embodiment the first circumferential edge 22 can be regarded as an inner circumferential edge, whilst the other, second circumferential edge 21 can be regarded as an outer circumferential edge. As is clearly shown in the figures, said second, folded-over circumferential edge 21, which lies substantially flat against the skin's surface, is folded over in outward direction in this embodiment.

It will be understood that, conversely, in another embodiment (not shown), the first circumferential edge 22, which abuts the skin substantially at right angles, surrounds the second circumferential edge 21, which lies substantially flat against the skin's surface. The second, folded-over circumferential edge 21, which lies substantially flat against the skin's surface, is folded over in inward direction (to within the interior of the flask-like container 11) in that case. In this embodiment (not shown) the first circumferential edge 22 can be regarded as an outer circumferential edge, whilst the other, second circumferential edge 21 can be regarded as an inner circumferential edge.

With regard to the location (inner or outer) of the two circumferential edges of the two above-described embodiments it will be apparent that the first circular circumferential edge 22 and the second circular circumferential edge 21 of the circular flexible collar 20 enclose an air chamber 23 the moment the rinsing device 10 is placed on the skin's surface surrounding the stoma wound with the circular flexible collar 20 thereof. Because the first circular circumferential edge 22 abuts the skin's surface substantially at right angles (or otherwise with a slight inclination), a first inner seal is realised.

By pressing the container 10 lightly against the skin's surface, a small amount of air can escape between the skin's surface and the folded-over external flanged edge 21 from the air chamber 23 enclosed by the two circumferential edges 21 and 22 and the skin's surface. In this way an underpressure is realised in the air chamber 23 thus formed, as a result of which the container 10 is sucked tightly against the skin. The advantageous result of this is that on the one hand shifting of the device 10 relative to the stoma wound is made more difficult, which makes it significantly easier for the patient to handle the container 10 during the cleaning session. In addition to that, the underpressure in the enclosed air chamber 23 ensures that the container 10 abuts the skin's surface over the entire circumferential edge of the circular flexible court 20, so that leakage along the circumferential edge 20 cannot occur.

In the latter case, all the dirty rinse water can be discharged via the outlet opening 11b and the discharge hose 16.

Figure 3:
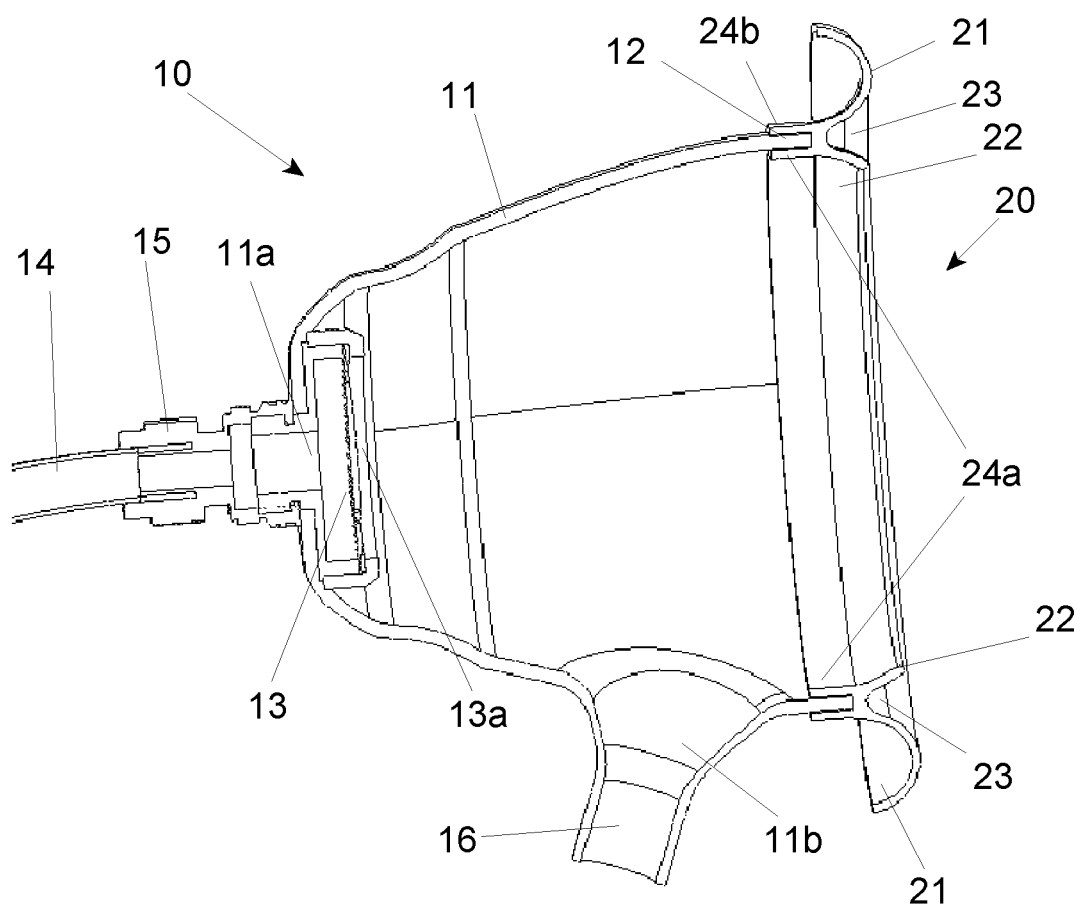
FIG. 3 is yet another view of the embodiment shown in FIG. 1.

As is clearly shown in the cross-sectional view of FIG. 3, the inner circumferential edge 22 is more or less straight, so that it abuts the skin's surface substantially at right angles. Said first circumferential edge may be slightly curved, if desired. Likewise, the second external circumferential edge is configured as a folded-over flanged edge, which will lie substantially flat against the skin's surface when the container is placed on the body. In addition to an additional seal that is thus realised, the flat abutting orientation of the second folded-over flanged edge 21 on the skin's surface allows a small amount of trapped air to escape from the enclosed air chamber 20 when the device 10 is lightly pressed against the skin.

The latter makes it possible to realise a slight underpressure in the air chamber and closed by the two circumferential edges 21 and 22 (and the skin's surface). The underpressure thus realised causes the container 10 to be sucked lightly against the skin's surface over the entire circumference thereof, so that the skin's surface is completely sealed, with the advantages already described in the foregoing for the user.

The circular flexible collar 20 is furthermore provided with two upright enclosing edges 24a-24b extending parallel to each other, between which the circumferential edge 12 of the flask-like container 11 is accommodated. Although the circular flexible collar 20 can thus be provided with a clamped fit over the circumferential edge 12 while still being detachable, in another embodiment the circular flexible collar 20 can form a fixed part of the flask-like container.

Such a combination can be made in one piece, using an injection-moulding process, wherein different materials for the container 11 and the column 20 can be used, which materials differ from each other as regards their hardness. The collar may be made of silicone, for example.

Figure 4:
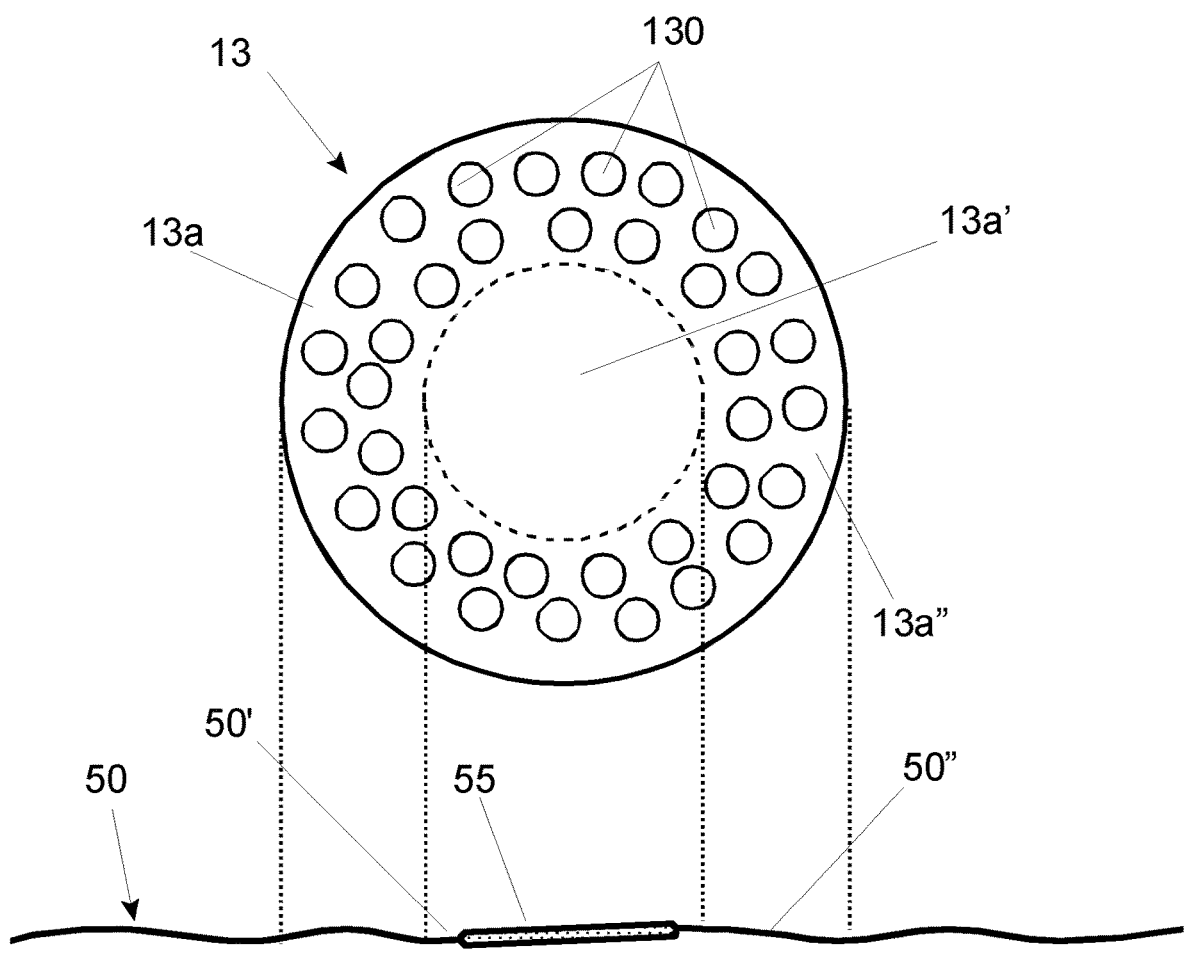
FIG. 4 is a detail view of the embodiment shown in FIG. 1.

In FIG. 4 yet another aspect of the device for cleaning a stoma is disclosed. The inlet opening 11a is provided with a nozzle 13 having an outflow surface 13a that is provided with a large number of openings 130. According to the prior art, these openings are evenly distributed over the entire outflow surface 13a.

According to the invention and as shown in FIG. 4, the outlet openings 130 are arranged in a concentric ring 13a' along the outer circumference of the outflow surface 13a. As clearly shown in FIG. 4, the outflow surface 13a has a central part 13a', in which no outlet openings are provided.

Thus, only the skin 50" surrounding the stoma wound will be directly sprayed with water jets from the outlet openings 130 if the container at 10 is correctly placed on a patient's skin surrounding the stoma wound 55. This is advantageous because the surrounding skin 50" is often soiled by faecal matter and adhesive residue from the stoma dressing (flange)—this in contrast to the area 50' of the stoma wound 55—so that a direct cleaning action can be realised.

Furthermore, patients find it uncomfortable and undesirable when water is directly sprayed on their stoma wound (50'-55). An additional advantage is that as a result of the concentric distribution of the outlet openings 130 in a concentric ring 13a" along the outer circumference of the outflow surface 13a, the skin's surface 50" directly surrounding the stoma wound 55 is massaged by the exiting water jets. Massaging the surrounding skin 50" stimulates the blood flow thereof and reduces the risk of necrosis or skin irritation.

The concentric ring 13a" provided with the outlet openings 130 preferably has a surface area in the order of 30-50%, in particular 35-45%, of the total surface area of the outflow surface 13a.

The outflow surface 13a preferably has a circular cross-section, but also a rectangular shape and an oval shape are possible. The configuration of the outflow surface 13a, and more specifically the form in which the nozzles 130 are distributed along the outer circumference of the outflow surface, can be geared to the shape of the stoma wound, which is not necessarily perfectly circular in shape at all times.

By giving the outflow surface 13a a convex shape, a larger area of the skin can be reached by the water jets. In a non-limitative embodiment, the convex outflow surface 13a has a diameter of about 50 mm, but as a result of the convex outflow surface an area of the skin having a diameter of about 115-120 mm can be covered. The diameter of the outlet openings 130 is about 0.4 mm.

It will be understood, however, that if children's stoma wounds are to be treated, smaller dimensions of the outflow surface 13a may be necessary.

It is noted that the invention also relates to a device for cleaning a stoma in a human or animal body that is not provided with a specific circular flexible collar provided around the circular contact edge, but only with an outflow surface 13a as described in the description, shown in the drawings and defined in the claims.

The invention claimed is:

1. A device for cleaning a stoma in a human or animal body, comprising:
    a container comprising:
        a lower opening comprising a circular contact edge configured to be placed over the stoma on the part of the body where the stoma is located;
        an inlet opening for connection to a water source; and
        an outlet opening for connection to a water drain,
        wherein the circular contact edge of the container comprises;
        a circular flexible collar comprising at least a first circumferential flange and a second circumferential flange; each having: an inner peripheral edge connected to the circular flexible collar and each also having a non-attached outer peripheral edge spaced apart relative to one another;
    the first and second circumferential flanges forming a recessed portion positioned there between that forms an air chamber that is configured to prevent rinse water leakage along the first and second circumferential flanges when the first and second circumferential flanges are placed on the body around the stoma while the device is in use; and
    wherein the second circumferential flange is flexible and is configured to provide a folded-over flanged edge, which is configured to abut the skin's surface around the stoma when placed on the body over the stoma.

2. The device according to claim 1, wherein, the first circumferential flange abuts the body substantially at right angles when placed on the skin's surface.

3. The device according to claim 1, wherein the first circumferential flange surrounds the second circumferential flange.

4. The device according to claim 1, wherein the second circumferential flange surrounds the first circumferential flange.

5. The device according to claim 1, wherein the inlet opening has an outflow surface provided with a plurality of openings.

6. The device according to claim 5, wherein the plurality of openings are arranged in a concentric ring along the outer circumference of the outflow surface, such that the plurality of openings direct rinse water adjacent to but not directly at the stoma while the device is in use.

7. The device according to claim 5, wherein the outlet openings take up surface area in the order of 30%-50% of the total surface area of the outflow surface.

8. The device according to claim 5, wherein the outflow surface is convex in shape.

9. The device according to claim 1, wherein the flexible collar is detachably provided on the circular contact edge.

* * * * *